US010364337B2

(12) United States Patent
Barman et al.

(10) Patent No.: US 10,364,337 B2
(45) Date of Patent: Jul. 30, 2019

(54) INHIBITION OF AMINE OXIDATION

(71) Applicant: Huntsman Petrochemical LLC, The Woodlands, TX (US)

(72) Inventors: Bhajendra Narayan Barman, Katy, TX (US); Robert A Grigsby, Jr., Spring, TX (US)

(73) Assignee: HUNTSMAN Petrochemical LLC, The Woodlands, TX (US)

( * ) Notice: Subject to any disclaimer, the term of this patent is extended or adjusted under 35 U.S.C. 154(b) by 0 days.

(21) Appl. No.: 14/997,845

(22) Filed: Jan. 18, 2016

(65) Prior Publication Data

US 2016/0130213 A1 May 12, 2016

Related U.S. Application Data

(62) Division of application No. 13/519,546, filed as application No. PCT/US2010/062476 on Dec. 30, 2010, now abandoned.
(Continued)

(51) Int. Cl.
| | |
|---|---|
| C08K 5/00 | (2006.01) |
| C08G 18/18 | (2006.01) |
| C08G 18/48 | (2006.01) |
| C08G 18/76 | (2006.01) |
| C07C 213/10 | (2006.01) |
| C08G 18/08 | (2006.01) |

(Continued)

(52) U.S. Cl.
CPC ............ *C08K 5/005* (2013.01); *C07C 213/10* (2013.01); *C08G 18/14* (2013.01); *C08G 18/1825* (2013.01); *C08G 18/1833* (2013.01); *C08G 18/40* (2013.01); *C08G 18/4841* (2013.01); *C08G 18/7671* (2013.01); *C08G 2101/0008* (2013.01); *C08G 2101/0083* (2013.01)

(58) Field of Classification Search
CPC ..... C08K 5/005; C08G 18/18; C08G 18/1816
See application file for complete search history.

(56) References Cited

U.S. PATENT DOCUMENTS

| | | | | | |
|---|---|---|---|---|---|
| 2,655,543 | A | * | 10/1953 | Linch ...................... | C08K 5/00 564/7 |
| 2,691,681 | A | * | 10/1954 | Linch .............................. | 564/7 |

(Continued)

FOREIGN PATENT DOCUMENTS

| | | |
|---|---|---|
| JP | S63-179917 A | 7/1988 |
| JP | H09-875 A | 1/1997 |

(Continued)

OTHER PUBLICATIONS

Alturfan, et al. "Investigation of Zinc and Copper Levels in Methimazole-Induced Hypothyroidism :Relation with the Oxidant-Antioxidant Status" Folia Biologica (Praha) 53, 183-188 (2007).

*Primary Examiner* — Michael L Leonard
(74) *Attorney, Agent, or Firm* — Huntsman Petrochemical LLC; Lewis Craft

(57) ABSTRACT

In an embodiment, an amine-oxidation inhibitor, such as a free radical scavenger and/or antioxidant, is added to an oxidation-sensitive amine, such as an amine catalyst, to inhibit oxidation of the amine. The inhibitor-treated amine may then be used in an application such as a polyurethane application to reduce the emission of undesired oxidation products from the polyurethane.

9 Claims, 12 Drawing Sheets

Related U.S. Application Data

(60) Provisional application No. 61/293,388, filed on Jan. 8, 2010.

(51) Int. Cl.
*C08G 18/40* (2006.01)
*C08G 101/00* (2006.01)

(56) References Cited

U.S. PATENT DOCUMENTS

| | | | |
|---|---|---|---|
| 3,072,582 A | 1/1963 | Bedell | |
| 3,091,551 A | 5/1963 | Robertson | |
| 3,112,281 A | 11/1963 | Gromacki et al. | |
| 3,577,556 A | 5/1971 | Longoria | |
| 3,931,060 A * | 1/1976 | Schubart | C08J 9/0014 521/115 |
| 4,021,385 A | 5/1977 | Austin et al. | |
| 4,156,759 A * | 5/1979 | Hostettler | C08G 18/6484 127/71 |
| 5,218,008 A * | 6/1993 | Parrish | C08K 5/1545 521/114 |
| 6,465,606 B2 | 10/2002 | Evans et al. | |
| 7,169,268 B2 | 1/2007 | Su et al. | |
| 2003/0109624 A1* | 6/2003 | Shah | C08G 18/12 524/492 |
| 2003/0212170 A1 | 11/2003 | Tinkl et al. | |
| 2005/0009938 A1 | 1/2005 | Ragsdale et al. | |
| 2008/0188326 A1 | 8/2008 | Wu et al. | |
| 2010/0168302 A1* | 7/2010 | Nagamori et al. | C08K 5/005 524/186 |
| 2010/0221474 A1 | 9/2010 | Prissok et al. | |

FOREIGN PATENT DOCUMENTS

| | | |
|---|---|---|
| JP | H11-142895 A | 5/1999 |
| JP | 2009-132841 A | 6/2009 |
| WO | 2001/59000 A | 8/2001 |
| WO | 2009010502 A | 1/2009 |
| WO | 2009/023130 A | 2/2009 |

\* cited by examiner

INHIBITION OF AMINE OXIDATION

CROSS REFERENCE TO RELATED APPLICATION

This application is a divisional of co-pending U.S. patent application Ser. No. 13/519,546, filed Jun. 27, 2012, which is the U.S. National Phase of International Application PCT/US2010/062476, filed Dec. 30, 2010, which designated the U.S. and which claims priority to U.S. Provisional App. Ser. No. 61/293,388, filed Jan. 8, 2010. The noted applications are incorporated herein by reference.

TECHNICAL FIELD

This invention relates generally to preventing the formation of or decreasing the presence of oxidation degradation products in oxidation-sensitive amines, and more particularly to preventing the formation of or decreasing the presence of formaldehyde and/or dimethylformamide in oxidation-sensitive amines.

BACKGROUND

Amines, such as amine catalysts that are useful in the polyurethane industry, may degrade over time or upon exposure to air. As the amines degrade, undesirable products such as formaldehyde and dimethylformamide (DMF), or both are produced. For instance, formaldehyde may be formed by oxidative demethylation of an amine and DMF may be obtained from certain tertiary amines by a similar oxidation process as is shown in FIG. 1. Formaldehyde and/or DMF from the amine may then be inadvertently incorporated into polyurethane or polyisocyanurate formulations and hence into the product of the formulation. Such products include insulation for buildings and appliances; flexible foams for beds, other furniture, and automobile seats; elastomers such as shoe soles, skate wheels, medical elastomers, and the like; urethane and/or urea coatings; and high-modulus urethane plastics such as furniture foam, molded doors, and rigid insulation panels just to name a few end products.

Both formaldehyde and DMF are linked to human health risks. Formaldehyde is a common indoor pollutant and may be toxic. Furthermore, it may cause allergic reactions in formaldehyde-sensitive people and it may be a human carcinogen. DMF is a possible carcinogen and is believed to cause birth defects. Thus, exposure to formaldehyde and DMF should be limited. Current short-term exposure limits, such as 15 minutes, for DMF and formaldehyde are 20 parts per million (ppm) and 2 ppm respectively and longer permissible exposure limits, such as eight hours, for DMF and formaldehyde are 10 ppm and 0.75 ppm respectively, as determined by the Occupational Safety and Health Administration (OSHA).

Depending upon the age of an oxidation-sensitive amine, DMF and formaldehyde may be found in relatively high amounts. Thus, there is a need for reduced concentrations of DMF and/or formaldehyde in oxidation-sensitive amines.

SUMMARY

In an embodiment of the present invention, an amine-oxidation inhibitor such as a free radical scavenger and/or an antioxidant is added to an oxidation-sensitive amine to inhibit oxidation of the amine. For example, when added to an oxidation-sensitive amine, such as an amine catalyst, the amine-oxidation inhibitor(s) may stop or reduce the formation of undesired amine oxidation products. In an embodiment, the free radical scavenger 1-methyl-3H-imidazole-2-thione (methimazole) may be added to an amine catalyst to stop or reduce dimethylformamide and/or formaldehyde formation. In other embodiments antioxidants and azoles (imidazole, substituted imidazoles, substituted benzothiazole and benzoxazole) may be used to obtain similar results.

DETAILED DESCRIPTION

Figure 1:
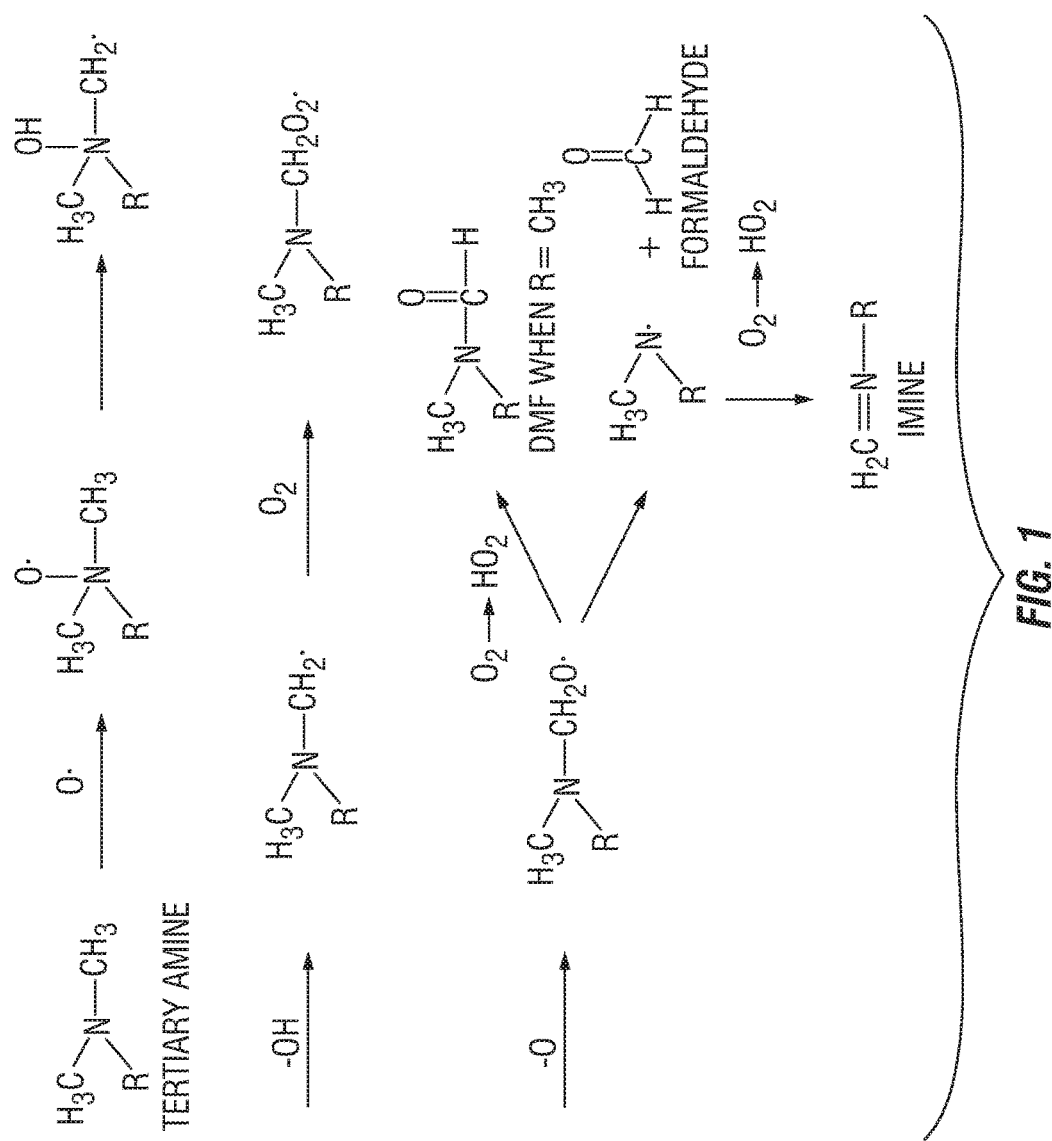
FIG. 1 shows possible pathways for forming amine oxidation products such as dimethylformamide and formaldehyde.
Figure 2:
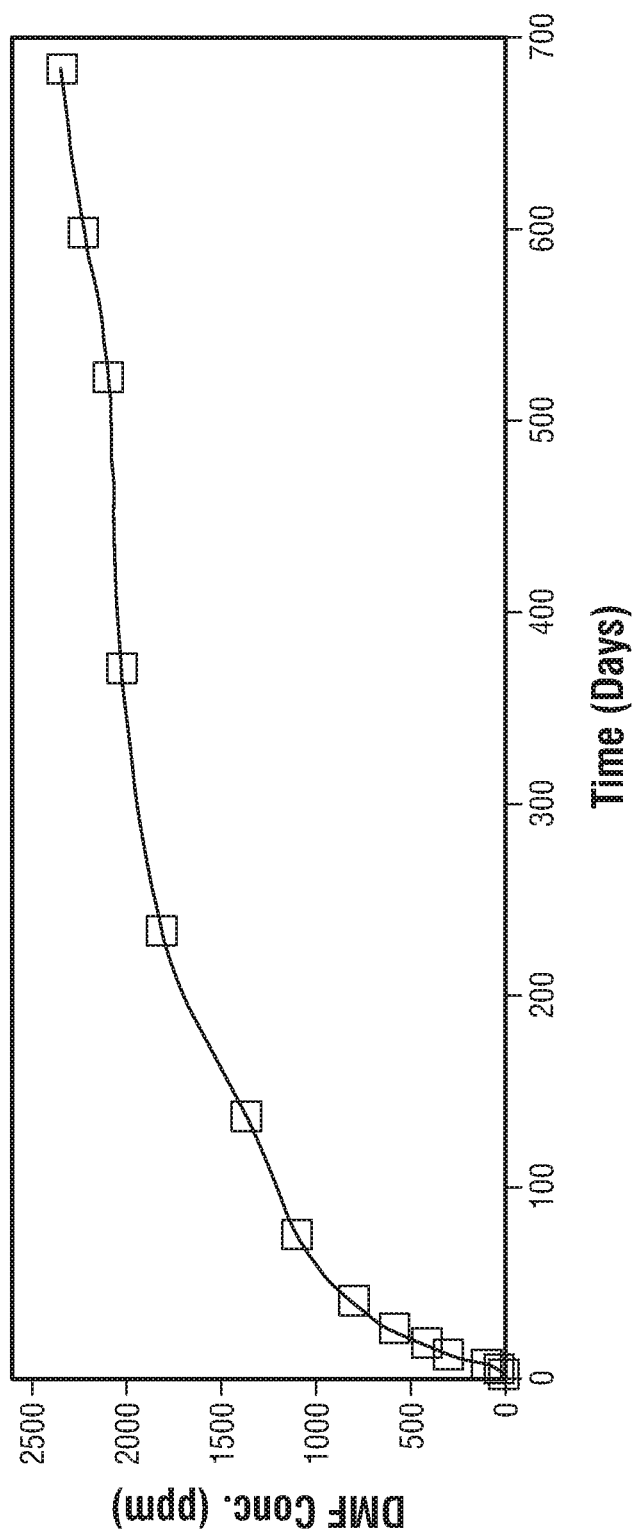
FIG. 2 is a graph that shows the time dependent increase of dimethylformamide at room temperature (~25° C.) in a sample of a tertiary amine catalyst.

Oxidation is a concern for some amine products. For instance, oxidation of urethane catalysts may lead to the production of undesirable oxidation products, which may reduce the shelf life and usability of the catalyst. Referring to FIG. 2, an untreated urethane catalyst, bis-(2-dimethylaminoethyl)ether (JEFFCAT® ZF-20), is oxidized in the presence of air at room temperature such that there is a constant increase of the oxidation product dimethylformamide (DMF) over time. For example, the concentration of DMF increased from the initial concentration of 14 ppm to 1378 ppm in 136 days, to 2026 ppm in 369 days, and to 2350 ppm in 682 days. Because DMF is banned at least in some countries, its production can limit product life and usability.

According to an embodiment of the present invention, an oxidation-sensitive amine is treated with an amine-oxidation inhibitor such as a free radical scavenger and/or an antioxidant to inhibit oxidation of the amine. As a result, amine oxidation products such as DMF and/or formaldehyde do not form or do not form as readily, which may increase the shelf-life and usability of the inhibitor-treated amine.

In another embodiment, such an inhibitor-treated amine may be added to other oxidation-sensitive materials such as polyols, isocyanates, blowing agents, and combinations thereof. The inhibitor-treated amine, other oxidation-sensitive material, or combinations thereof may then be used to make a product. As one example, the inhibitor-treated amine may be a urethane catalyst for use in the production of a polyurethane product. Using the inhibitor-treated amine ensures minimal amounts of DMF and/or formaldehyde in the urethane catalyst as well as in the urethane foam product or other urethane product.

The oxidation-sensitive amine may be any amine that is susceptible to oxidation. For example, the oxidation-sensitive amine may be one or more amine-containing catalysts that are useful in the production of polyurethanes, including polyurethane elastomers, and/or polyisocyanurates. Such oxidation-sensitive amine catalysts include tertiary amine-containing catalysts, amine catalysts that catalyze urethane or urea reactions, or both. Exemplary amine catalysts include, without limitation, tertiary amine catalysts such as bis-(2-dimethyaminoethyl)ether (JEFFCAT® ZF-20 catalyst), N,N,N'-trimethyl-N'-hydroxyethylbisaminoethylether (JEFFCAT® ZF-10 catalyst), N-(3-dimethylaminopropyl)-N,N-diisopropanolamine (JEFFCAT® DPA catalyst), N,N-dimethylethanolamine (JEFFCAT® DMEA catalyst), triethylene diamine (JEFFCAT® TEDA catalyst), blends of N,N-dimethylethanolamine and triethylene diamine (such as JEFFCAT® TD-20 catalyst), N,N-dimethylcyclohexylamine (JEFFCAT® DMCHA catalyst), benzyldimethylamine (JEFFCAT® BDMA catalyst), pentamethyldiethylenetriamine (JEFFCAT® PMDETA catalyst), N,N,N',N'',N''-pentamethyldipropylenetriamine (JEFFCAT® ZR-40 catalyst), N,N-bis(3-dimethylaminopropyl)-N-isopropanolamine (JEFFCAT® ZR-50 catalyst), N'-(3-(dimethylamino)propyl-N,N-dimethyl-1,3-propanediamine (JEFFCAT® Z-130 catalyst), 2-(2-dimethylaminoethoxy)ethanol (JEFFCAT® ZR-70 catalyst), N,N,N'-trimethylaminoethyl-ethanolamine (JEFFCAT® Z-110 catalyst), N-ethylmorpholine (JEFFCAT® NEM catalyst), N-methylmorpholine (JEFFCAT® NMM catalyst), 4-methoxyethylmorpholine, N,N'dimethylpiperzine (JEFFCAT® DMP catalyst), 2,2'dimorpholinodiethylether (JEFFCAT® DMDEE catalyst), 1,3,5-tris(3-(dimethylamino)propyl)-hexahydro-s-triazine (JEFFCAT® TR-90 catalyst), 3-(2-(dimethylamino)ethoxy)propylamine, and combinations thereof. The aforementioned JEFFCAT® catalysts are available from Huntsman Petrochemical LLC, The Woodlands, Tex.

In other embodiments, the oxidation-sensitive amine may be one or more of a polyetheramine, ethyleneamine, alkoxylated amine, and surfactant amine, although embodiments are not so limited. Suitable polyetheramines include monoamines such as JEFFAMINE® M-1000 amine, JEFFAMINE® M-2005 amine, and JEFFAMINE® M-2070 amine; diamines such JEFFAMINE® D-230 amine, JEFFAMINE® D-400 amine, and JEFFAMINE® D-2000 amine; polyether diamines such as JEFFAMINE® HK-511 amine, JEFFAMINE® ED-600 amine, JEFFAMINE® ED-900 amine, and JEFFAMINE® ED-2003 amine; unhindered diamines such as JEFFAMINE® EDR-104 amine, JEFFAMINE® EDR-148 amine, and JEFFAMINE® EDR-176 amine; triamines such as JEFFAMINE® T-403 amine, JEFFAMINE® T-3000 amine, and JEFFAMINE® T-5000 amine; and mixtures of polyether monoamines and diamines such as aminated triethyleneglycol (e.g. JEFFAMINE® XTJ-512 amine), and the like; suitable ethyleneamines include ethylenediamine (EDA), diethylenetriamine (DETA), triethylenetetramine (TETA), tetraethylenepentamine (TEPA), aminoethylpiperzine (AEP), aminoethylethanolamine (AEEA), pentaethylenehexamine (PEHA), hexaethyleneheptamine (HEHA), and mixtures thereof; suitable alkoxylated amines include 2-(2-aminoethoxy)ethanol (DGA® amine), diethanolamine (DEA), N-methyldiethanolamine (MDEA), triethanolamine (TEA), and the like; and suitable surfactant amines include hydrophobic polyether monoamines such as SURFONAMINE® B-100 amine and SURFONAMINE® B-200 amine, and hydrophilic polyether monoamines such as SURFONAMINE® L-100 amine, SURFONAMINE® L-200 amine, SURFONAMINE® L-207 amine, SURFONAMINE® L-300 amine, and the like. JEFFAMINE® products, SURFONAMINE® products, and DGA® product are available from Huntsman Petrochemical LLC, The Woodlands, Tex.

The amine-oxidation inhibitor may be any suitable inhibitor such as an antioxidant and/or free radical scavenger. Suitable amine-oxidation inhibitors include those that are compatible with, and that can inhibit oxidation of, one or more amines such as amine catalysts, polyetheramines, ethyleneamines, alkoxylated amines, and/or surfactant amines, although embodiments are not limited thereto. In an embodiment the amine-oxidation inhibitor may be one or more free radical scavengers such as methimazole, phenyl methimazole, and derivatives thereof; allupurinol, propyl thiouracil, glutamine, diaminobenzylamine, and nicotinamide to name a few. Other suitable amine-oxidation inhibitors may be one or more antioxidants that are compatible with an oxidation-sensitive amine, such as an amine catalyst, and that can suppress free-radical-mediated DMF and/or formaldehyde formation. The antioxidants may be hindered phenolics such as butylated hydroxy toluene, IRGASTAB® PUR 68 antioxidant, IRGANOX® 1010 antioxidant, IRGANOX® 1135 antioxidant, and IRGANOX® 1076 antioxidant; hindered aliphatic amines such as TINUVIN® 770 light stabilizer; hindered aromatic amines such as IRGASTAB® PUR 55 antioxidant, IRGANOX® 5057 antioxidant, and NAUGARD® 445 antioxidant; mixed phenolics and amines such as IRGANOX® MD 1024 antioxidant and IRGANOX® 565; antioxidants with triazole and phenolic groups such as TINUVIN® P antioxidant, TINUVIN® 234 antioxidant, TINUVIN® 327 antioxidant, and TINUVIN® 328 antioxidant; proprietary antioxidants such as TINUVIN® 866 antioxidant; and natural antioxidants such as Vitamin C, Vitamin E and/or glutathione, although embodiments are not limited to these exemplary antioxidants. Furthermore, in some embodiments, the amine-oxidation inhibitor may be a combination of one or more free radical inhibitors and antioxidants. IRGASTAB®, IRGANOX®, and TINUVIN® products are available from Ciba Specialty Chemical Corporation, Tarrytown, N.Y., and NAUGARD® products are available from Chemtura Corporation, Middlebury, Conn.

Azoles such as substituted imidazoles, arylimidazoles have been found to show inhibitory activity toward hydroxylation and N-demethylation. These inhibitors may be imidazole, 2-mercaptoimidazole, 2-mercaptobenzimidazole, 2-mercaptobenzothiazole, 2-mercaptobenzoxazole, triazole and substituted triazoles, although embodiments are not limited to these exemplary azoles.

The oxidation-sensitive amine may be treated with the amine-oxidation inhibitor at any time. For example, in some embodiments the amine-oxidation inhibitor may be added to the oxidation-sensitive amine just before use or any other point where exposure to air is possible. Alternatively, the amine-oxidation inhibitor may be added to the oxidation-sensitive amine at production, for storage. In a particular embodiment, the container in which the inhibitor-treated amine is stored is padded with an inert gas. In a preferred embodiment, the headspace of the container holding an inhibitor-treated amine may be padded with nitrogen for better stability. These examples are nonlimiting and an amine-oxidation inhibitor may be added to an oxidation-sensitive amine at any time and in any manner.

The amount of amine-oxidation inhibitor added to an oxidation-sensitive amine may be any effective amount. For example, in some embodiments, the oxidation-sensitive amine may be treated with 5 ppm, 10 ppm, 100 ppm, 250 ppm, 1000 ppm, or 5000 ppm of an amine-oxidation inhibitor, and all amounts there between. In other embodiments, an amine-oxidation inhibitor may be added to an oxidation-sensitive amine to form a blend where the amount of amine-oxidation inhibitor in the blend is from 0.5% to 10% by weight of the total blend. In an embodiment, the afore-mentioned blend may be used as a concentrate to enable customization to a desired inhibitor concentration level. For example, the concentrated blend may be mixed with an untreated oxidation-sensitive amine to reach a desired amine-oxidation inhibitor level. These examples are also non-limiting and the amount of amine-oxidation inhibitor used to treat a particular oxidation-sensitive amine may be adjusted according to factors such as the type of amine, estimated storage time, and application. The temperature and pressure at which the amine-oxidation inhibitor is effective may depend on various factors including the amount of amine-oxidation inhibitor used to treat the oxidation-sensitive amine. Generally, the amine-oxidation inhibitor may be effective at temperatures from 0° C. to 150° C. and at pressures up to 200 psi (pounds per square inch). In some embodiments, the amine-oxidation inhibitor is especially effective at 25° C., 40° C., or 70° C. and ranges there between.

In another embodiment, an inhibitor-treated amine (e.g. an amine that has been treated with a suitable amine-oxidation inhibitor) may be added to other oxidation-sensitive materials. In a particular embodiment, an inhibitor-treated amine may be added to one or more components for making a polyurethane product, a polyisocyanurate product, or any other polyurethane products. Generally, a polyurethane product (or a polyisocyanurate product) may be formed by reacting an isocyanate component with a polyol component. One or more inhibitor-treated amines such as an amine catalyst may be added to the isocyanate component, the polyol component, or both. Additionally or alternatively, the inhibitor-treated amine may be added to one or more sub-components, such as blowing agents, additives, or auxiliary agents, which may then be added to the polyol component and/or the isocyanate component. As such, resultant polyurethane/polyisocyanurate products may contain reduced oxidation products such as DMF, formaldehyde, or both, which means that less of these oxidation products may be emitted from the product.

The isocyanate component may be any isocyanate or combinations of isocyanates known in the field of polyurethanes and/or polyisocyanurates. Examples of such isocyanates include, without limitation, toluenediisocyanate (TDI), methylenediphenyldiisocyante (MDI), higher functional (greater than 2) methylenediphenyldiisocyanates (poly MDI or pMDI), and pre-polymers/quasi-prepolymers of these isocyanates. In some embodiments, an inhibitor-treated amine such as an inhibitor-treated amine catalyst may be added to the isocyanate component. In a particular embodiment, the inhibitor-treated amine catalyst is an inhibitor-treated urethane catalyst.

The polyol component may include any polyol or combinations of polyols that are useful in the fields of polyurethanes/polyisocyanurates. For example, the polyol component may include polyether polyols, polyester polyols, any other polyol, and combinations of polyols. Furthermore, the polyols may be made from mono-, di-, tri-, or higher functional initiators and they may include alkylene oxides such as ethylene oxide, propylene oxide, butylene oxide and/or any combination of these or other oxides. An example of polyether polyols includes polyoxypropylene and/or polyoxyethylene polyols, and an example of polyester polyols includes aromatic polyester polyols and/or aliphatic polyester polyols. Particularly useful polyols include propylene glycol initiated polyols such as JEFFOL® PPG-2000 polyol, propylene oxide-ethylene oxide co-polymers such as JEFFOL® G-31-28 polyol and JEFFOL® PPG-3706 polyol, polyether polyols such as VORANOL® 4701 polyol and VORANOL® 4702 polyol. JEFFOL® products may be obtained from Huntsman International LLC, The Woodlands, Tex.; VORANOL® products may be obtained from Dow Chemical Company, Midland, Mich.

The polyol component may also include one or more low molecular weight chain extenders, crosslinking agents, or mixtures of chain extenders and crosslinking agents. Chain extenders may include alkane diols, dialkylene glycols, polyalkylene polyols, and combinations thereof, and cross-linking agents may include ethanediols, butanediols, hexanediols, heptanediols, octanediols, nonanediols, diethylene glycol, dipropylene glycol, polyoxyalkylene glycols, and combinations thereof.

In some embodiments, an inhibitor-treated amine such as an inhibitor-treated amine catalyst may be added to one or more polyols of the composition. In a particular embodiment, the inhibitor-treated amine catalyst is an inhibitor-treated urethane catalyst.

In some embodiments, a blowing agent may be added to the isocyanate component or the polyol component. Furthermore, the blowing agent may or may not have an inhibitor-treated amine added thereto. The blowing agent may be any blowing agent or combination of blowing agents useful in the art of polyurethanes and/or polyisocyanurates. Generally, such blowing agents include water, physical blowing agents, and chemical blowing agents, which may be used alone or in combinations. Exemplary blowing agents include, but are not limited to, water, pentane, cyclopentane, butane, FORANE® 141B agent, which is available from Arkema Inc. (Philadelphia, Pa.), and HFC-245FA, which is available from Honeywell International Inc. (Morristown, N.J.).

Typically, the polyol component may include additives and/or auxiliary agents. Exemplary additives and/or auxiliary agents include film stabilizers, cell regulators, flame retardants, plasticizers, fillers, pigments, surfactants, and the like, or any combination thereof. To the extent that an additive or auxiliary agent is an oxidation-sensitive amine, an amine-oxidation inhibitor may be added to such additive or auxiliary agent.

The polyurethanes or polyisocyanurates may be made using any technique. For instance, a polyurethane or polyisocyanurate may be formed by separately blending the components of the polyol component and the isocyanate component, either or both of which may include an inhibitor-treated catalyst and/or other inhibitor-treated amine. Once separately blended, the two components may be mixed by any means known in the art. For example, the polyol component and the isocyanate component may be mixed to facilitate the manufacture of a molded product or a product made without a mold.

Embodiments however are not limited to polyurethanes and/or polyisocyanurates; the inhibitor-treated amine may be used in any application where free radical mediated oxidation may occur. Furthermore, there is no restriction on when the inhibitor-treated amine may be added to another oxidation-sensitive material; however, it may be beneficial to add the inhibitor-treated amine before storing the other oxidation-sensitive material or just before its use. Likewise, there may be a wide range of temperatures at which an inhibitor is effective such as temperatures from 0° C. to 150° C., and pressures may be up to 200 psi.

EXAMPLES

The following non-limiting examples are provided to further illustrate embodiments described herein. The examples, however, are not intended to be all-inclusive and are not intended to limit the scope of the embodiments described herein.

Example 1

In Examples 1a-1c, DMF and formaldehyde concentrations were tracked in samples of a tertiary amine mixed with methimazole (MM). Generally, 50 ml each of 10, 100, 250, and 1000 ppm methimazole (an amine-oxidation inhibitor) solutions were prepared with bis-(2-dimethyaminethyl)ether (JEFFCAT® ZF-20 amine catalyst, available from Huntsman Petrochemical LLC, The Woodlands, Tex.). Methimazole is available from Sigma-Aldrich Corp., St. Louis, Mo.

An 8 ml aliquot from each of the foregoing preparations was poured in a corresponding 20 ml vial and an 8 ml aliquot of untreated JEFFCAT® ZF-20 amine catalyst was poured in a separate 20 ml vial. Thus, there were five 20 ml vials in a set; at least one sample per set had 0, 10, 100, 250, or 1000 ppm methimazole. Sets of samples were incubated at 25° C., 40° C., or 70° C. Periodically, a portion of each sample (about 0.4 ml) was withdrawn to determine the concentration of DMF and/or formaldehyde formed in that sample. DMF and formaldehyde concentrations were determined by high performance liquid chromatography with a UV detector.

Example 1a

In this example, DMF and formaldehyde concentrations were tracked in a set of samples that were incubated at room temperature (about 25° C.) for up to 680 days. Sample 1a (Neat ZF-20) was a control sample having no methimazole, and samples 2a, 3a, 4a, and 5a were test samples, which included 10, 100, 250, and 1000 ppm of methimazole, respectively. Prior to incubation, baseline DMF and formaldehyde concentrations were determined. Thereafter, for each sample in the set, DMF and formaldehyde concentrations were periodically determined.

Figure 3:
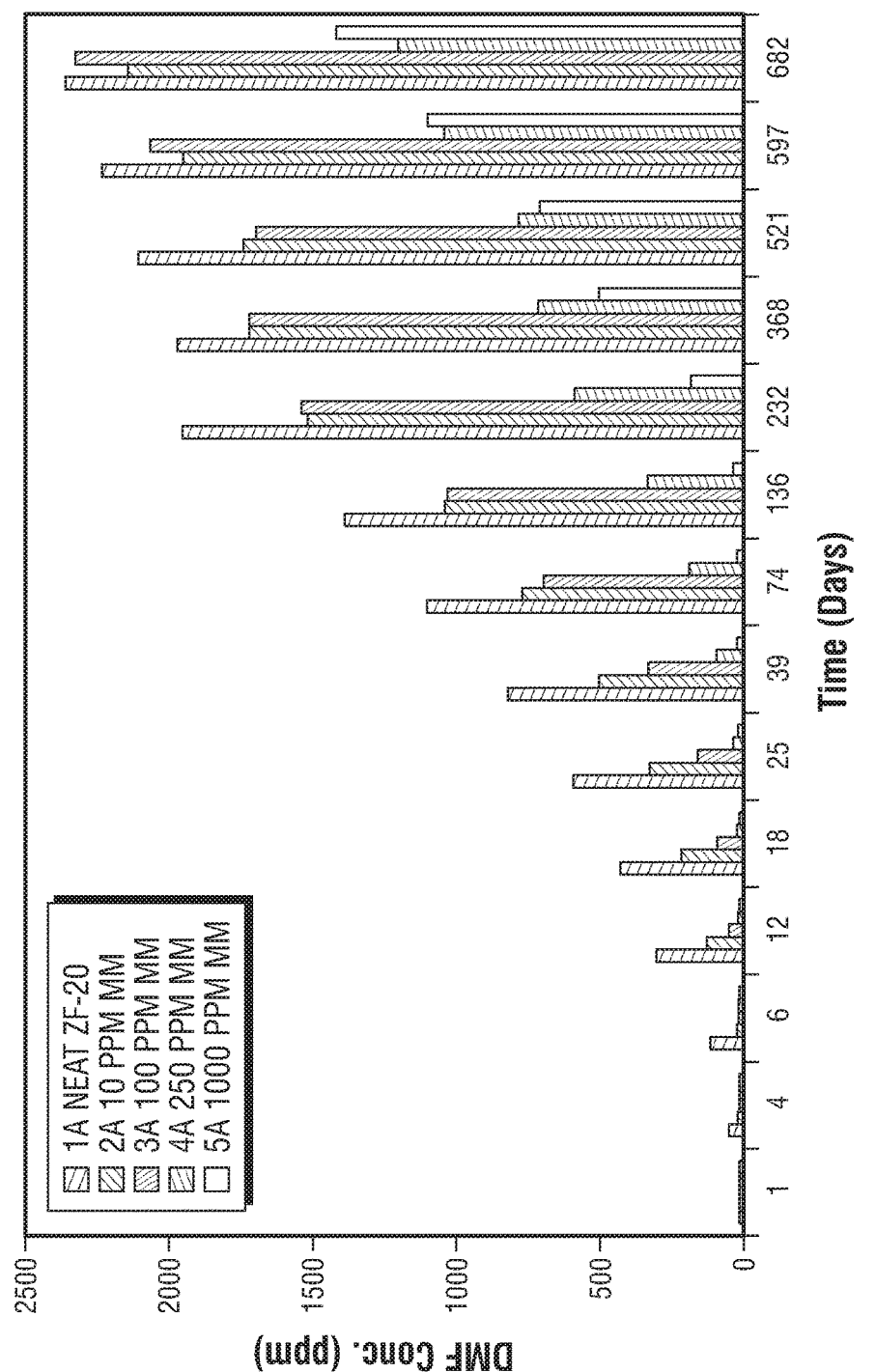
FIG. 3 is a graph which shows the effect of various concentrations of a free radical scavenger on dimethylformamide formation in samples that were incubated for up to 682 days at 25° C.

Referring to FIG. 3, DMF concentrations (ppm) at different time-points are shown for samples 1a-5a. After about 1 day (18 hours) of incubation, the samples do not show an appreciable difference in DMF accumulation. Thereafter, however, the DMF concentration in sample 1a began to rise compared to the test samples, and by 12 days and thereafter the difference in DMF concentration between control sample 1a and the test samples was quite dramatic. This is especially true for the difference in DMF concentrations between sample 1a and samples 4a and 5a.

Referring to Table 1 below, DMF concentrations (in ppm) for samples 1a, 4a, and 5a are shown. The initial DMF content for these samples was 14 ppm. After incubating at 25° C. for 39 days, however, the DMF concentration in sample 1a rose to 812 ppm, and for samples 4a and 5a the DMF concentrations were less than 100 ppm and less than 25 ppm, respectively. Thus, at this time point much less DMF was formed in test samples 4a and 5a as compared to the control sample 1a. Similarly, after incubating for 136 days the DMF content in sample 1a rose to 1378 ppm (about 100 fold from the initial concentration) whereas it was only 337 ppm and 35 ppm in samples 4a and 5a respectively. Similarly, after 232 days, the DMF contents of samples 4a and 5a were 588 ppm and 184 ppm, respectively, compared to 1940 ppm for control sample 1a. Thus, at 25° C., which is about room temperature, samples with methimazole, especially those samples with 250 and 1000 ppm methimazole, had lower DMF concentrations compared to the control sample with no methimazole. Referring to Table 1 and FIG. 3, this trend continued for all time points up to 682 days. However, DMF concentration from samples 5a was found to approach that from sample 4a at 521 days and eventually, DMF concentrations were higher for sample 5a compared to sample 4a at time points of 597 days and 682 days.

TABLE 1

| Sample | Methimazole (ppm) | Initial DMF (ppm) | 39 days (ppm) | 136 days (ppm) | 232 days (ppm) | 369 days (ppm) | 682 days (ppm) |
| --- | --- | --- | --- | --- | --- | --- | --- |
| 1a | 0 | 14 | 812 | 1378 | 1940 | 2026 | 2350 |
| 4a | 250 | 14 | 97 | 337 | 588 | 710 | 1197 |
| 5a | 1000 | 14 | 21 | 35 | 184 | 503 | 1411 |

Referring to Table 2 below, it was observed that the free radical scavenger methimazole also prevented formaldehyde build-up in samples 4a and 5a (compared to control sample 1a). For example, the initial formaldehyde content in samples 1a, 4a, and 5a was 50 ppm. After incubating at 25° C. for 521 days, however, control sample 1a had 772 ppm formaldehyde and test samples 4a and 5a had 538 ppm and 580 ppm formaldehyde, respectively. After being incubated for 682 days at 25° C., the formaldehyde concentration for samples 4a increased to 548 ppm, but still well below the formaldehyde concentration of the control sample at 851 ppm. However, formaldehyde concentration of 782 ppm for the sample 5a was close to that of the control sample at this time point.

TABLE 2

| Sample | Methimazole (ppm) | Initial Formaldehyde (ppm) | 521 days (ppm) | 682 days (ppm) |
|---|---|---|---|---|
| 1a | 0 | 50 | 772 | 851 |
| 4a | 250 | 50 | 538 | 548 |
| 5a | 1000 | 50 | 580 | 782 |

The amounts of methimazole remaining in the samples after being incubated for 136 days, 232 days, 368 days and 682 days at 25° C. were also determined. Similar to DMF, methimazole was determined by high performance liquid chromatography with UV detection. Referring to Table 3, samples 2a and 3a, which initially included 10 and 100 ppm methimazole respectively, were both methimazole-free after 136 days. In contrast, samples 4a and 5a still had 30 ppm and 760 ppm methimazole, respectively remaining after 136 days. Additional losses of methimazole from samples 4a and 5a were observed after 232 days. After 682 days, sample 5a was left with only 70 ppm of methimazole down from 1000 ppm.

TABLE 3

| Sample | Initial Methimazole (ppm) | 136 days (ppm) | 232 days (ppm) | 369 days (ppm) | 682 days (ppm) |
|---|---|---|---|---|---|
| 2a | 10 | 0 | 0 | 0 | 0 |
| 3a | 100 | 0 | 0 | 0 | 0 |
| 4a | 250 | 30 | 21 | 20 | 5 |
| 5a | 1000 | 760 | 637 | 435 | 70 |

Example 1b

In this example, a set of samples was analyzed for the presence of DMF after being incubated in an oven at 40° C. for a total of 39 days. Sample 1b was a control sample having no methimazole and samples 2b, 3b, 4b, and 5b were test samples, which included 10, 100, 250, and 1000 ppm of methimazole, respectively.

Figure 4:
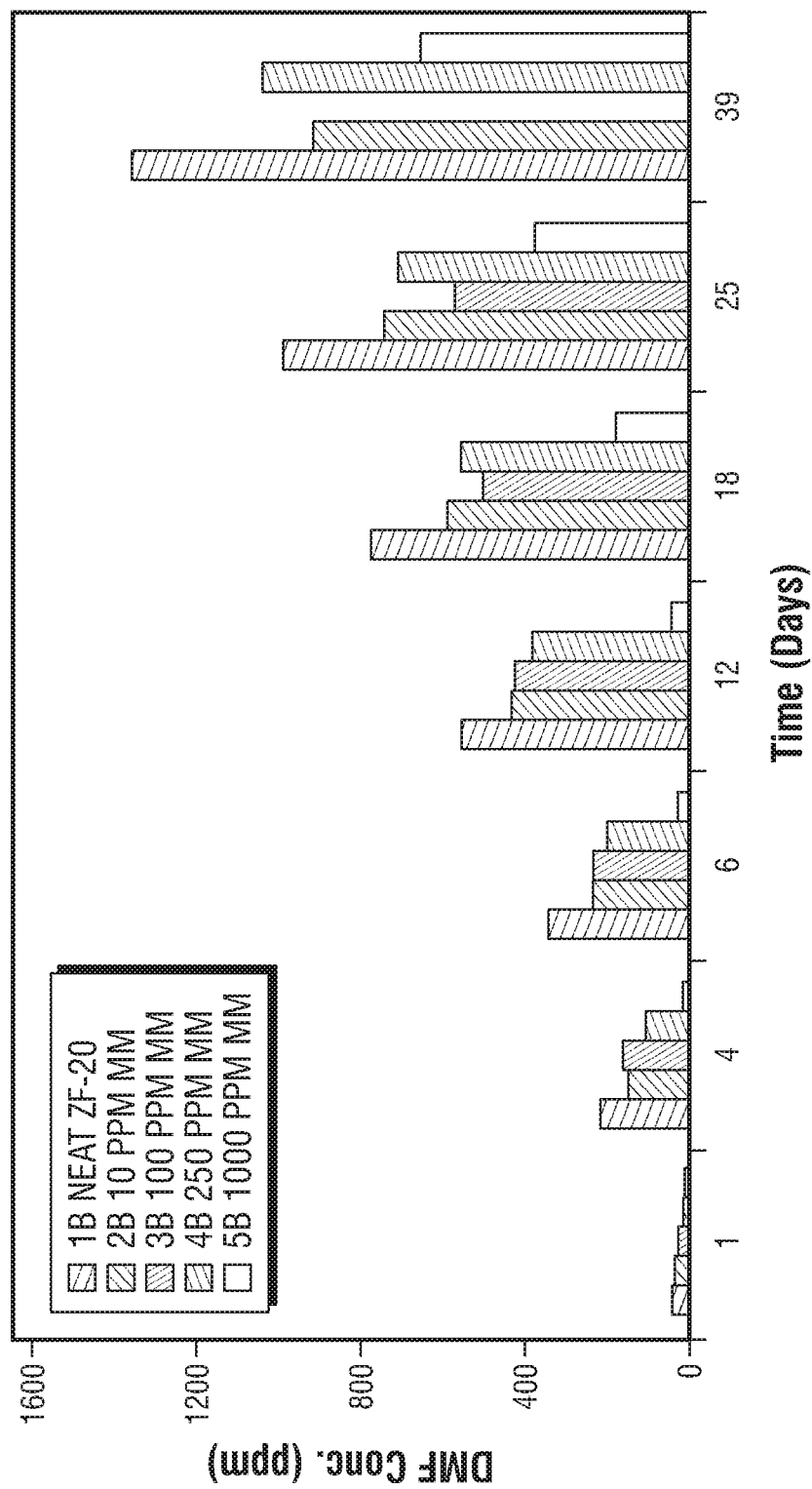
FIG. 4 is a graph which shows the effect of various concentrations of a free radical scavenger on dimethylformamide formation in samples that were incubated for up to 39 days at 40° C.

Referring to FIG. 4, DMF concentrations in samples 1b-5b are shown. As with the control sample 1a, control sample 1b showed a steady increase of DMF concentration over the 39 days. In contrast, samples 2b-5b had a reduced DMF formation over time compared to the control 1b. The most effective concentration of methimazole at 40° C. was 1000 ppm. Interestingly, sample 4b, which included 250 ppm methimazole, did not appear to be as effective at 40° C. at or after 18 days of incubation as sample 3b, which included 100 ppm methimazole.

Example 1c

In this example, a set of catalyst samples was analyzed for the presence of DMF after being incubated in an oven at 70° C. for a total of 39 days. Sample 1c was a control catalyst sample having no methimazole and catalyst samples 2c, 3c, 4c, and 5c were test catalyst samples, which, in addition to the amine catalyst, included 10, 100, 250, and 1000 ppm of methimazole, respectively.

Figure 5:
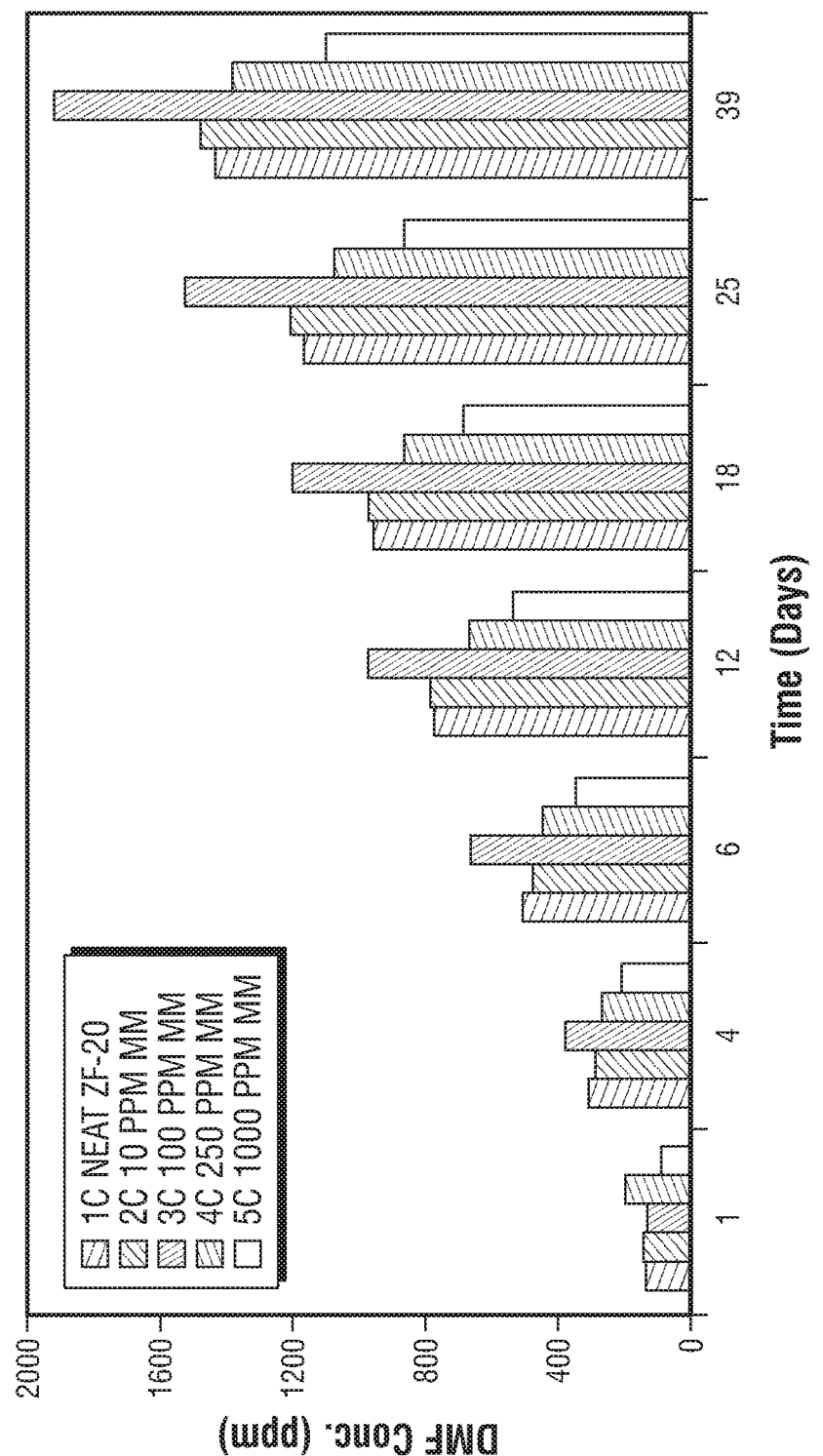
FIG. 5 is a graph that shows the effect of various concentrations of a free radical scavenger on dimethylformamide formation in samples that were incubated for up to 39 days at 70° C.

Referring to FIG. 5, DMF concentrations in catalyst samples 1c-5c are shown. As with the other control samples, control sample 1c showed a steady increase in DMF formation over the 39 day incubation period. The methimazole in samples 2c and 3c did not affect DMF formation at this temperature. In fact, DMF formation in sample 3c, which included 100 ppm methimazole, was greater than control (1c) at most time points. DMF formation in sample 4c (250 ppm methimazole), however, was usually less than the control sample at the various time points. As with the other temperatures, the sample having 1000 ppm methimazole (5c) showed the biggest reduction in DMF formation over the entire incubation period as compared to the control 1c.

It should be noted that the data obtained for Examples 1b and 1c had a higher level of uncertainty, which was believed to be due to evaporation loss of some DMF. The evaporation loss was measured by weighing sample before placing the sample in the oven and after taking it out from the oven and cooling. Typical evaporation losses were found to be 0.2% and 0.4% at 40° C. and 70° C., respectively.

Example 2

In this example, aldehyde emissions from flexible foams were determined. Generally, a control foam and a test foam were made using the same formula:

TABLE 4

| Component | Weight % |
|---|---|
| EO-capped Polyol of MW 6000 | 58.75 |
| Water | 2.36 |
| JEFFCAT ® ZF-10 catalyst | 0.05 |
| JEFFCAT ® DPA catalyst | 0.6 |
| Silicone surfactant | 0.5 |
| Stabilizer (diethanolamine) | 0.24 |
| Isocyanates (MDI) | 37.5 |
| Total | 100.0 | wherein the catalyst used in the control foam was methimazole-free and the catalyst used in the test foam contained 1000 ppm methimazole. In the above formulation, JEFFCAT® ZF-10 catalyst and JEFFCAT® DPA catalyst are tertiary amines, and serve as reactive catalysts. These are available from Huntsman Petrochemical LLC, The Woodlands, Tex.

Before use in the foam formulation, catalysts for the test foam were prepared by adding enough methimazole to each of the JEFFCAT® ZF-10 catalyst and the JEFFCAT® DPA catalyst to give 1000 ppm methimazole per catalyst. The concentrations of aldehydes and ketone in JEFFCAT® ZF-10 catalyst prior to adding methimazole were as follows: formaldehyde 46 ppm, acetaldehyde 41 ppm, acetone 0.1 ppm, propionaldehyde 1.1 ppm, and butyraldehyde 0 ppm. The corresponding concentrations for JEFFCAT® DPA catalyst were as follows: formaldehyde 12 ppm, acetaldehyde 9.3 ppm, acetone 6.0 ppm, propionaldehyde 22 ppm, and butyraldehyde 0 ppm. Catalysts for the control foam were from the same catalyst batches as that of the test foam, but without having any free radical scavenger added thereto.

Generally, the foams were made by mixing the polyol, water, respective catalysts, silicone surfactant, and stabilizer in a mixing cup for 24 seconds. Thereafter, the isocyanate was added to the polyol mixture, which was then stirred for 6 seconds and poured into a block mold 65 cm×60 cm×10 cm. The foams were allowed to cure for 3 minutes at 60° C.

The foam blocks were then tested for aldehyde emission in a manner similar to ASTM D-5116-06. For this, a model VCE 1000 instrument from Votsch Industrietechnik (Germany) was used for environmental chamber testing. The size of the chamber was 1000 liter. The sample size was one piece of 65 cm×60 cm×10 cm foam block. The temperature of the chamber was maintained at 65° C. and the humidity was maintained at 50%. The zero air exchange rate was 400 L/h. Volatile aldehydes given off by the foam were drawn at the exhaust flow outlet through a 2,4-dinitrophenylhydrazine (DNPH)-coated silica gel cartridge using a sampling pump for 5 hours. After sample collection, aldehydes were eluted from each DNPH cartridge with 5 ml acetonitrile and determined by HPLC-UV detection.

Referring to Table 5 below, the presence of formaldehyde, acetaldehyde, propionaldehyde, and butyraldehyde was evaluated in both the control and test foam samples. As compared to the control foam, the concentration of each gas was less in the test foam. Thus, free radical scavenger added to catalyst samples also has a beneficial affect on the foams made from such catalysts.

TABLE 5

| Foam Sample | Formaldehyde ($\mu g/m^3$) | Acetaldehyde ($\mu g/m^3$) | Propionaldehyde ($\mu g/m^3$) | Butyraldehyde ($\mu g/m^3$) |
|---|---|---|---|---|
| Control | 85 | 18 | 108 | 38 |
| Test | 20 | 3 | 29 | 14 |

Example 3

In Examples 3a-3b, DMF and formaldehyde concentrations were tracked in samples of a tertiary amine, JEFFCAT® ZF-20 mixed with antioxidants. Generally, 25 ml each of 200 ppm, and 1000 ppm antioxidant solutions were prepared with JEFFCAT® ZF-20 amine catalyst. Untreated JEFFCAT® ZF-20 (Neat ZF-20) was used as control sample. As antioxidants, IRGANOX® 1010 (Irg 1010), IRGANOX® MD 1024 (MD 1024), TINUVIN® 866 (Tin 866), TINUVIN® 328 (Tin 328), and TINUVIN® 770 (Tin 770) were studied. These were available from Sigma-Aldrich Corp., St. Louis, Mo. In FIGS. 6 to 9, these antioxidants are referred to by abbreviations shown in parentheses.

An 8 ml aliquot from each of the foregoing preparations was poured in a corresponding 20 ml vial and an 8 ml aliquot of untreated JEFFCAT® ZF-20 amine catalyst was poured in a separate 20 ml vial. Thus, there were two 20 ml vials for each antioxidant; for example, Irg 1010, 200 ppm and Irg 1010, 1000 ppm are two solutions with 200 ppm and 1000 ppm of IRGANOX® 1010 antioxidant, respectively. Thus, there were eleven sample solutions in each set of samples. Sets of samples were incubated at 25° C. and 40° C. Periodically, a portion of each sample (about 0.4 ml) was withdrawn to determine the concentration of DMF and/or formaldehyde formed in that sample. DMF and formaldehyde concentrations were determined by high performance liquid chromatography with a UV detector.

Example 3a

Figure 6:
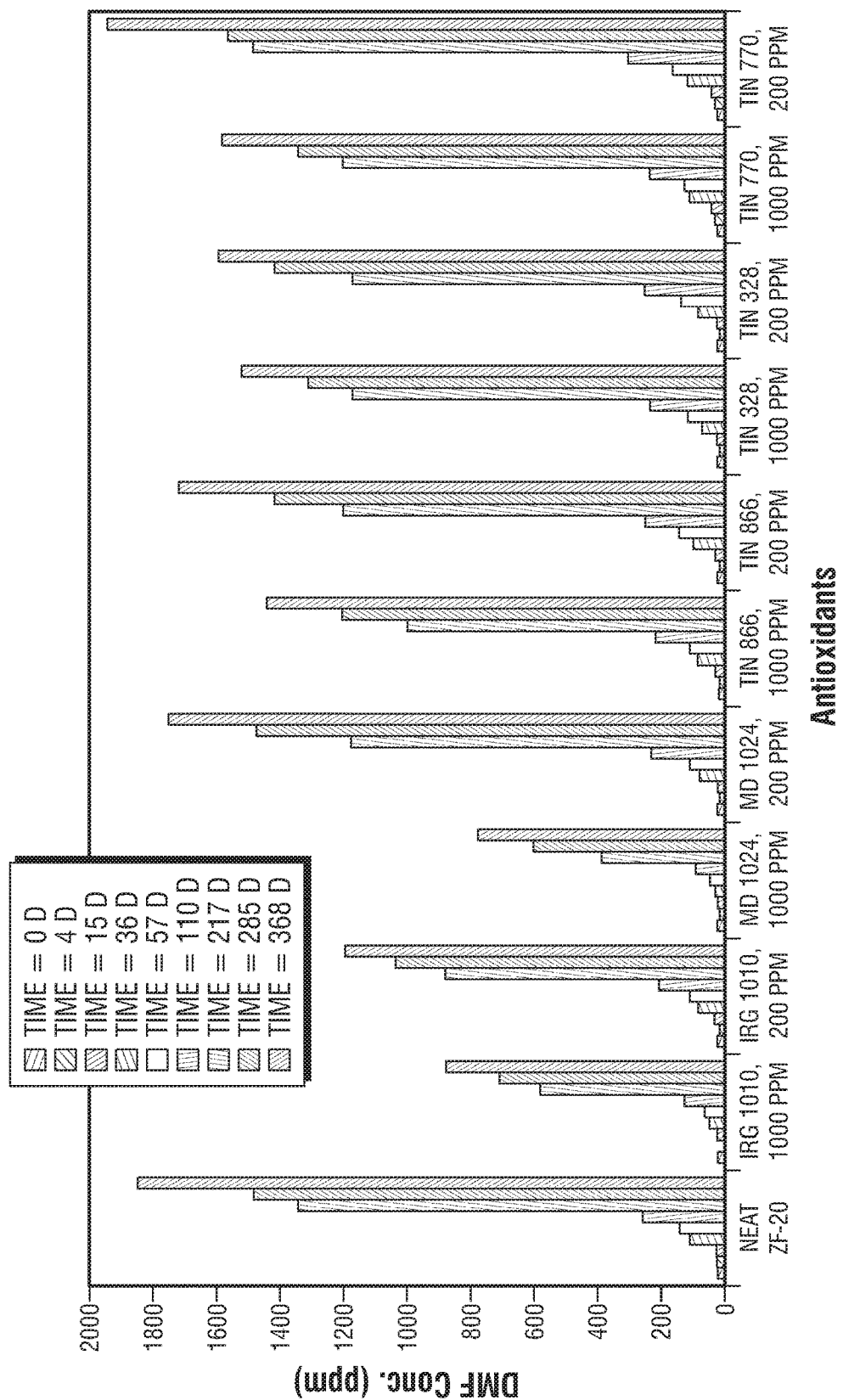
FIG. 6 is a graph showing the effects of two concentrations of several antioxidants on dimethylformamide formation in samples that were incubated for up to 368 days at 25° C.

Referring to FIG. 6, DMF concentrations at different time-points and at 25° C. are shown for a set of eleven sample solutions. The initial DMF concentration in JEFFCAT® ZF-20 was 18.9 ppm. The DMF concentrations in samples Neat ZF-20, Tin 770, 200 ppm and Tin 770, 1000 ppm began to rise faster than other test samples after 4 days. Thereafter the difference in DMF concentration between control sample and the test samples was quite significant. Almost at all time points, the lowest DMF concentrations were observed in samples with 1000 ppm IRGANOX® MD 1024, followed by 1000 ppm IRGANOX® 1010 and 200 ppm IRGANOX® 1010. However, this study for 368 days suggests that all solutions except two TINUVIN® 770 solutions, produced lower DMF amounts compared to the control sample.

Figure 7:
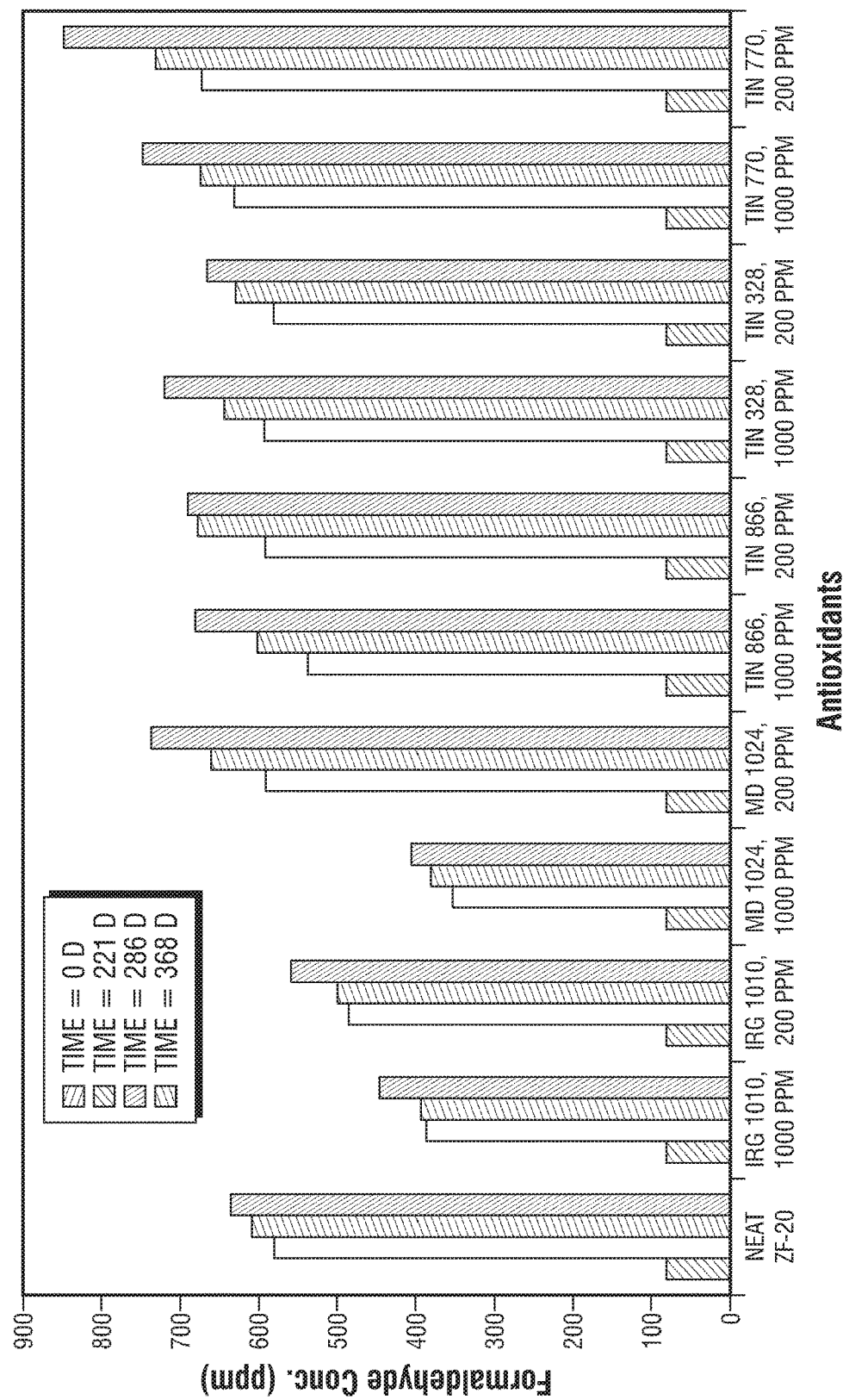
FIG. 7 is a graph showing the effects of several antioxidants on formaldehyde formation in samples that were incubated for up to 368 days at 25° C.

Referring to FIG. 7, a study with antioxidants for a period of 368 days, showed that two antioxidants IRGANOX® 1010 and IRGANOX® MD 1024 can provide reduced formaldehyde build-up compared to the control sample. Both antioxidants at 1000 ppm, and Irg 1010 at 200 ppm were found to be effective.

Example 3b

Figure 8:
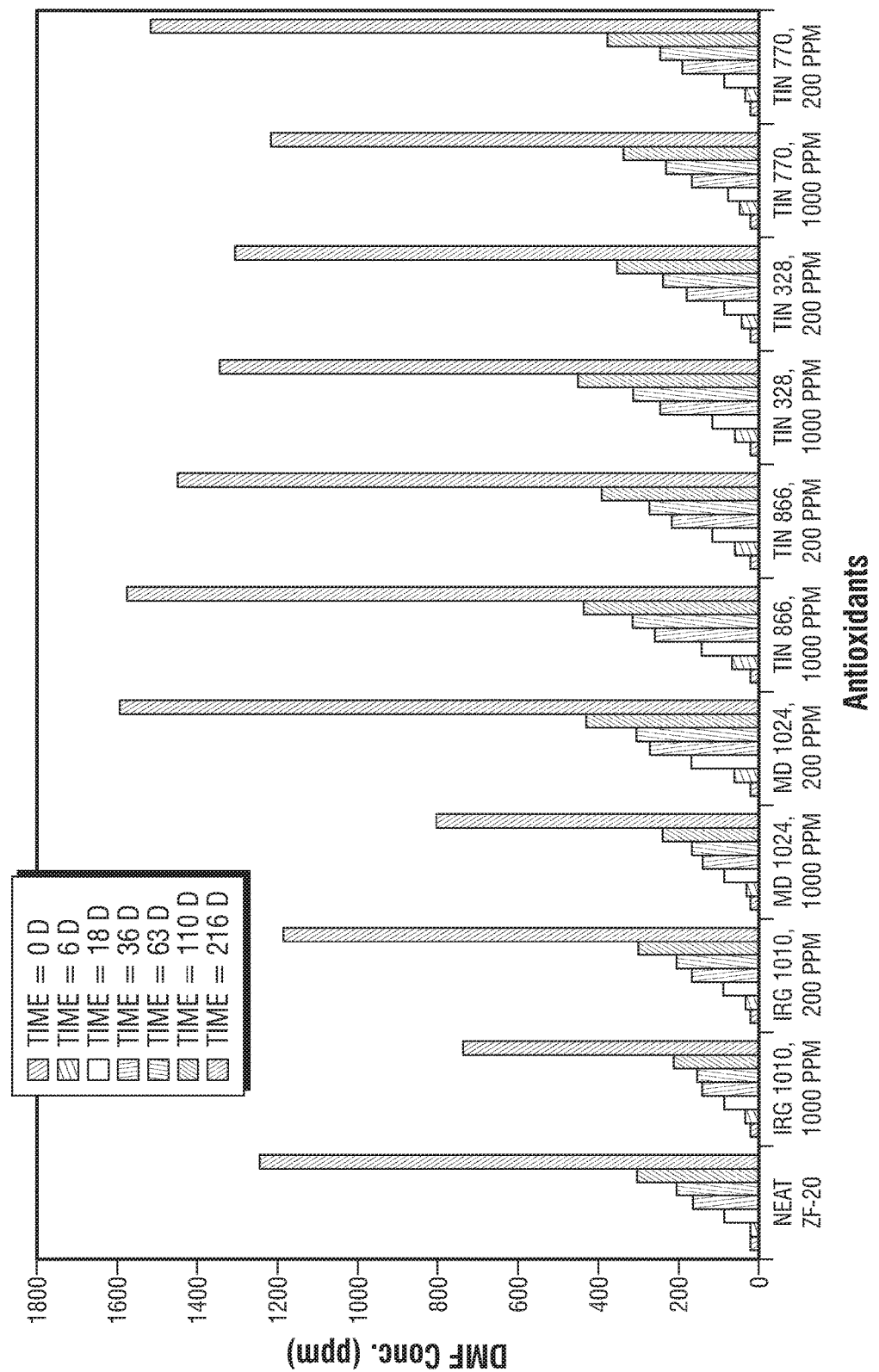
FIG. 8 is a graph showing the effects of several antioxidants on dimethylformamide formation in samples that were incubated for up to 216 days at 40° C.

Referring to FIG. 8, the second set of samples was analyzed for the presence of DMF after being incubated in an oven at 40° C. for a total of 216 days. Here, DMF concentrations remain relatively low at 163 ppm or less for a period of 18 days. Thereafter, as with the control sample, all samples showed a steady increase of DMF concentration. However, samples Irg 1010, 1000 ppm and MD 1024, 1000 ppm had reduced DMF formation over time compared to the control sample.

Figure 9:
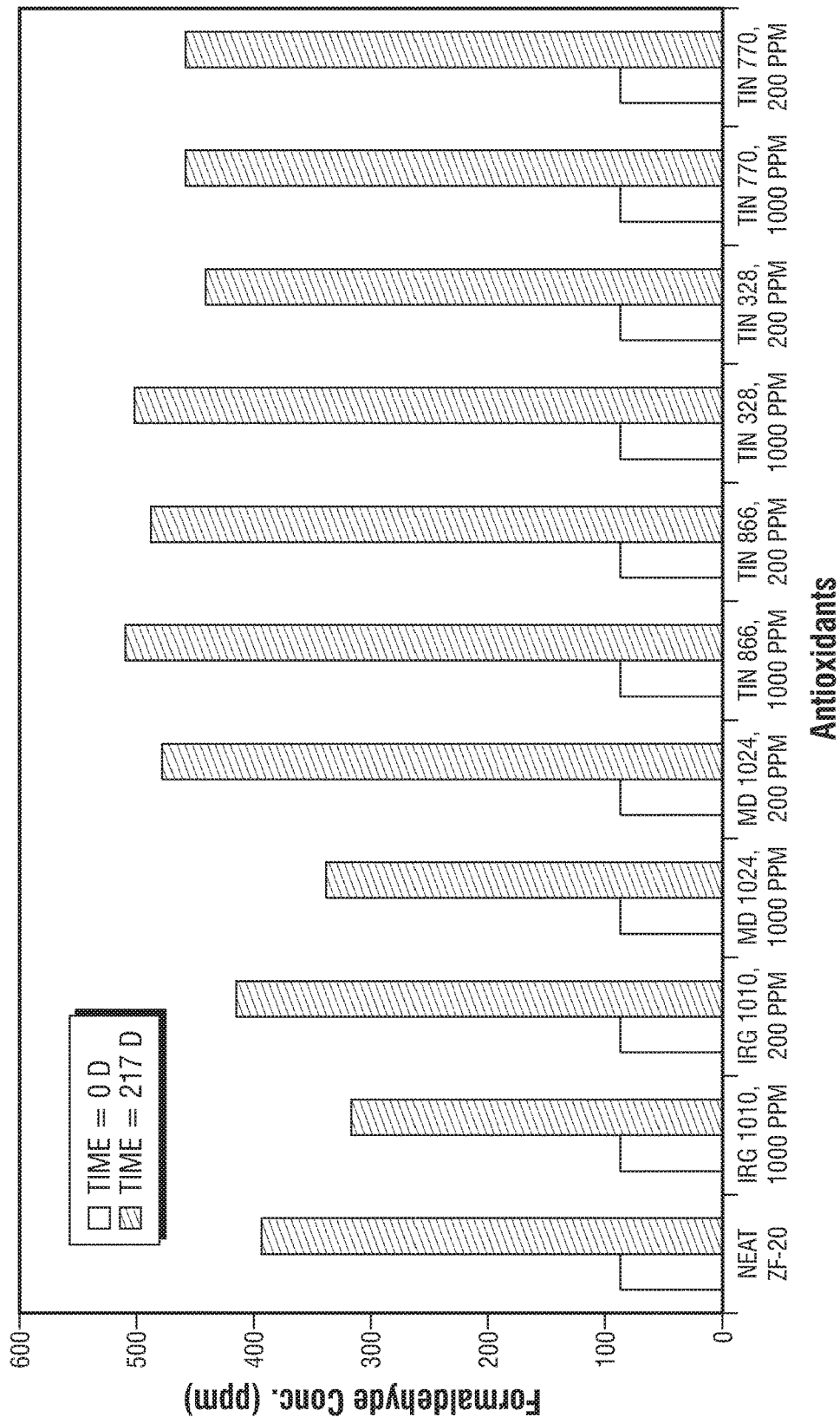
FIG. 9 is a graph that shows the effects of several antioxidants on formaldehyde formation in samples that were incubated for 217 days at 40° C.

Referring to FIG. 9, formaldehyde concentrations were measured for all samples incubated in an oven for 217 days. The formaldehyde concentrations in JEFFCAT® ZF-20 at the end of the incubation period showed that Irg 1010, 1000 ppm and MD 1024, 1000 ppm were effective in slowing down formaldehyde formation in the amine catalyst.

Example 4

Figure 10:
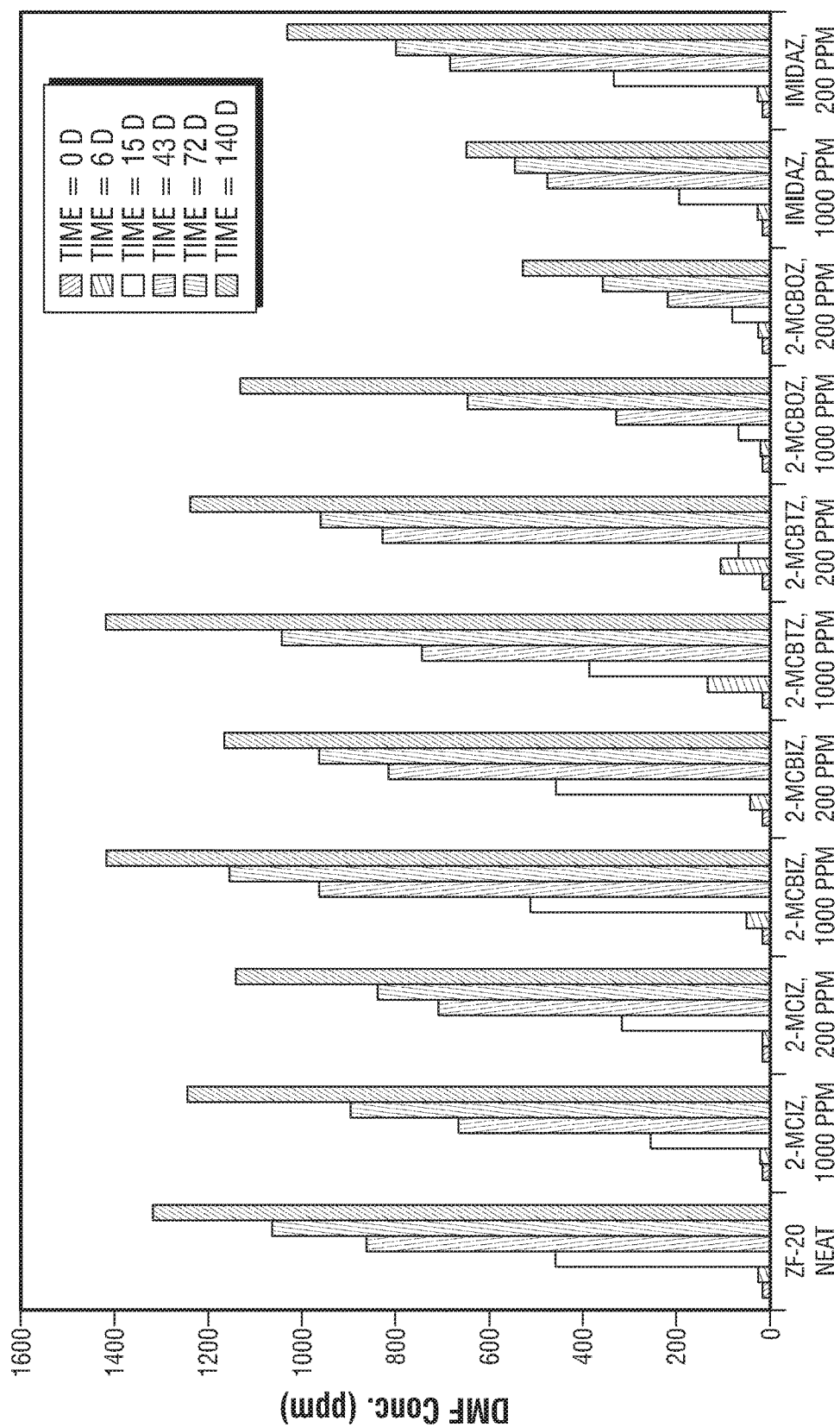
FIG. 10 is a graph that shows the effects of two concentrations of several azoles on dimethylformamide formation in samples that were incubated for up to 140 days at 25° C.
Figure 11:
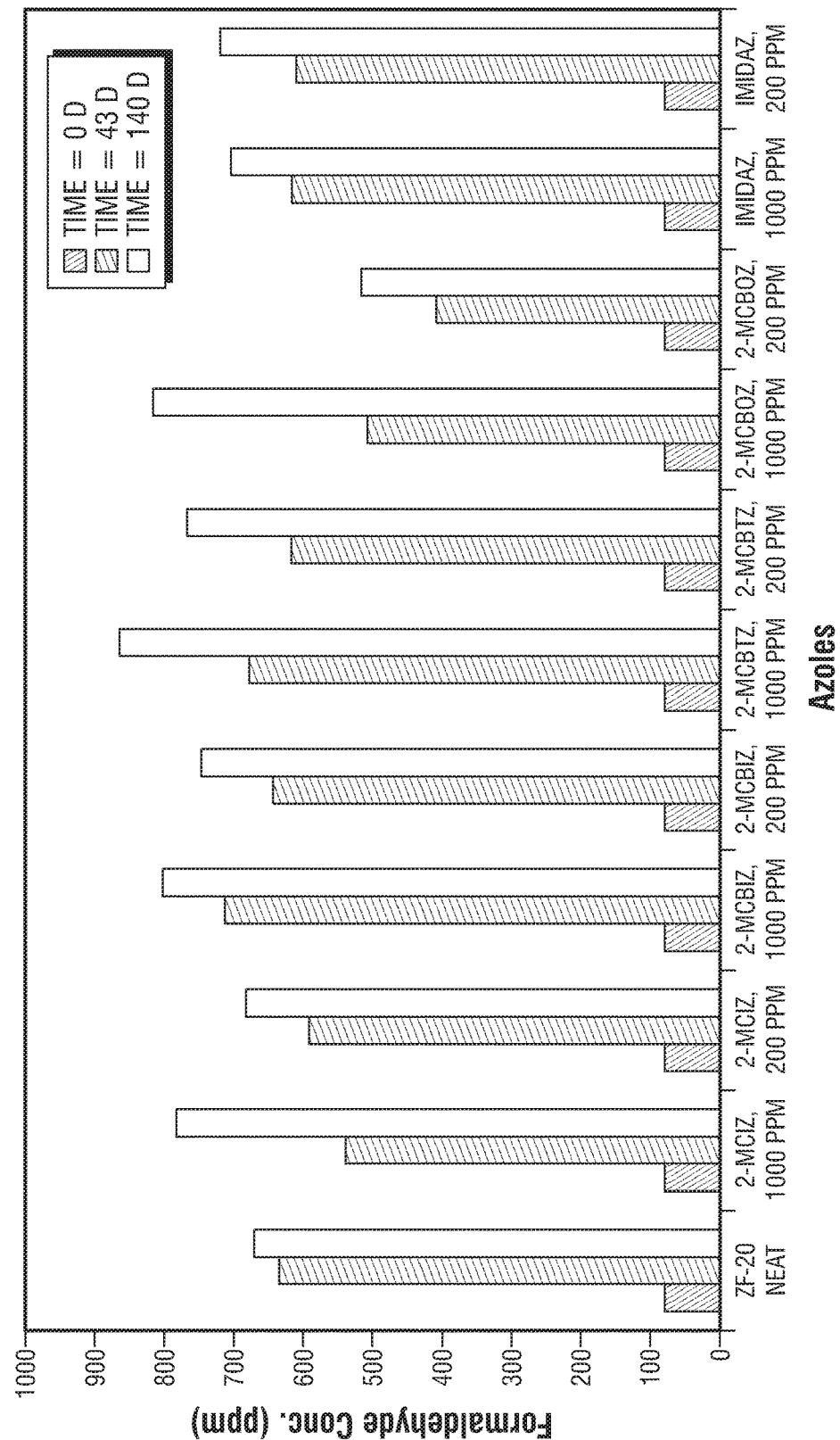
FIG. 11 is a graph that shows the effects of several azoles on formaldehyde formation in samples that were incubated for up to 140 days at 25° C.
Figure 12:
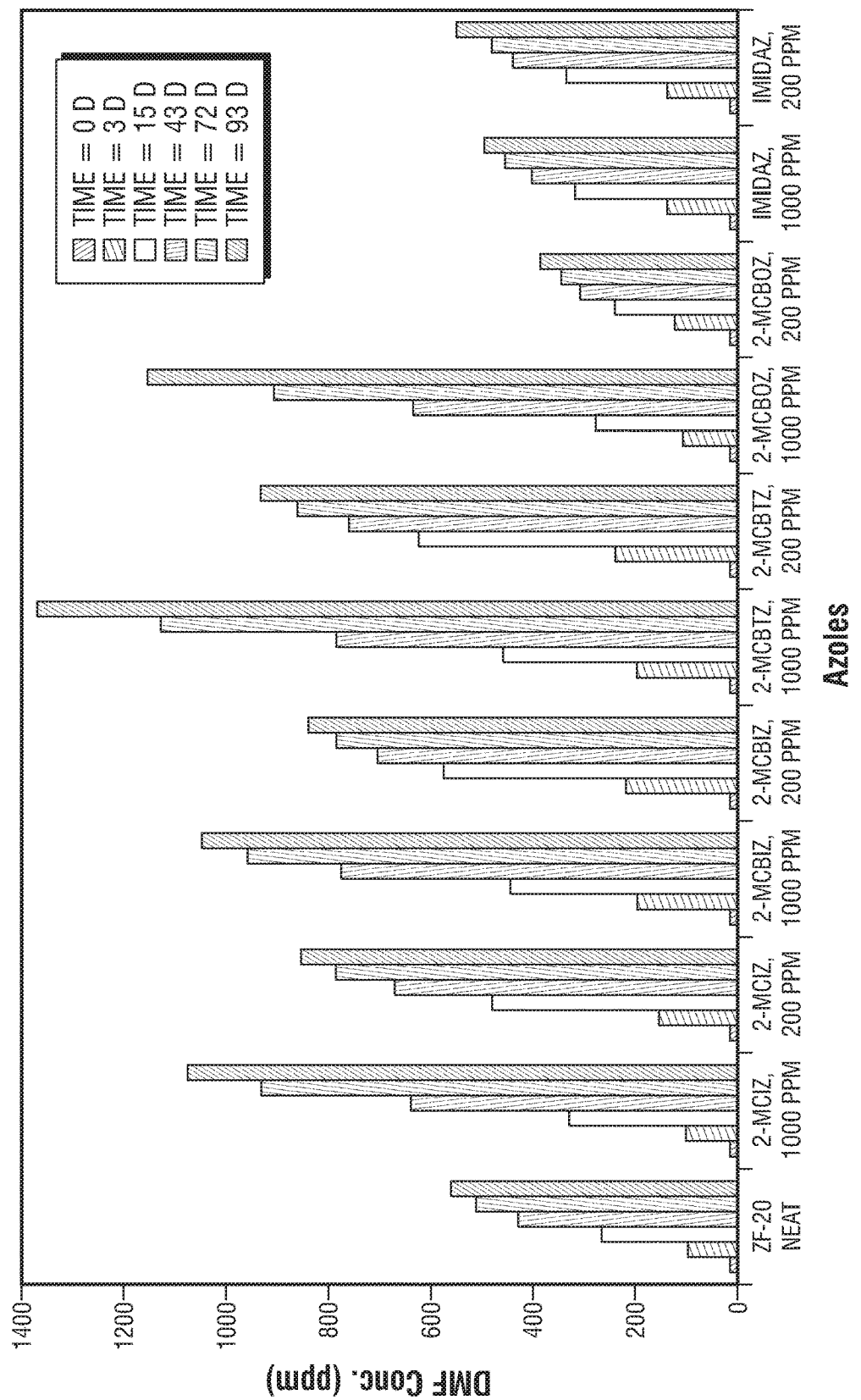
FIG. 12 is a graph which shows the effects of several azoles on dimethylformamide formation in samples that were incubated for up to 93 days at 40° C.

In Examples 4a and 4b, DMF and formaldehyde concentrations were tracked in samples of a tertiary amine, JEFFCAT® ZF-20, mixed with azoles. Generally, 25 ml each of 200 ppm, and 1000 ppm azole solutions were prepared with JEFFCAT® ZF-20 amine catalyst. Untreated JEFFCAT® ZF-20 (Neat ZF-20) was used as the control sample. The following azoles were studied: 2-mercaptoimidazole (2-MCIZ), 2-mercaptobenzimidazole (2-MCBIZ), 2-mercaptobenzothiazole (2-MCBTZ), 2-mercaptobenzoxazole (2-MCBOZ) and imidazole (IMIDAZ). These are available from Sigma-Aldrich Corp., St. Louis, Mo. In FIGS. 10 to 12, these azoles are referred to by abbreviations shown in parentheses.

An 8 ml aliquot from each of the azole preparations was poured in a corresponding 20 ml vial and an 8 ml aliquot of untreated JEFFCAT® ZF-20 amine catalyst was poured in a separate 20 ml vial. Thus, there were two 20 ml vials for each azole. For example, 2-MCIZ, 200 ppm and 2-MCIZ, 1000 ppm are two solutions with 200 ppm and 1000 ppm of 2-mercaptoimidazole, respectively. Thus, there were eleven sample solutions in each set of samples. Sets of samples were incubated at 25° C. and 40° C. Periodically, a portion of each sample (about 0.4 ml) was withdrawn to determine the concentration of DMF and/or formaldehyde formed in that sample. DMF and formaldehyde concentrations were determined by high performance liquid chromatography with a UV detector.

Example 4a

Referring to FIG. 10, DMF concentrations at different time-points up to 140 days and at 25° C. are shown for a set of eleven sample solutions. The initial DMF concentration in JEFFCAT® ZF-20 was 18.1 ppm. Compared to the control sample (Neat ZF-20) solution, 2-mercaptoimidazole, 2-mercaptobezoxazole and imidazole solutions showed reduced amounts of DMF. Both 2-mercaptobenzimidazole and 2-mercaptobenzothiazole provided comparable or higher DMF amounts as compared to the control sample at almost all time points Referring to FIG. 11, a study with azole solutions for a period of 140 days, suggests that formaldehyde data are scattered. However, 2-mercaptoimidazole, 2-mercaptobezoxazole and imidazole showed some advantages compared to the control sample Example 4b Referring to FIG. 12, the second set of samples was analyzed for the presence of DMF after being incubated in an oven at 40° C. for a total of 93 days. Here, DMF concentrations increased steadily in all solutions. However, samples 2-MCBOZ, 200 ppm and IMIDAZ 1000 ppm provided reduced DMF amounts compared to the control sample at all time points.

Example 5

In Example 5, a tertiary amine, JEFFCAT® ZF-20 sample in a 20 mL vial was stored for a period of 370 days at room temperature in a nitrogen box after blanketing with nitrogen. DMF and formaldehyde concentrations were measured at the start and at the end of the experiment. The initial DMF concentration was 18.9 ppm and that after 370 days was 36 ppm. The corresponding formaldehyde amounts are 60 ppm and 221 ppm, respectively.

The above disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A method of forming an inhibitor-treated amine comprising combining:
   (i) an oxidation-sensitive amine selected from one or more of a tertiary amine catalyst, a polyetheramine, an ethyleneamine, a surfactant amine, and an amine selected from 2-(2-aminoethoxy)ethanol, diethanolamine, N-methyldiethanolamine, and triethanolamine, with
   (ii) an amine-oxidation inhibitor, wherein the amine-oxidation inhibitor is a free-radical scavenger selected from one or more of allupurinol, propyl thiouracil, glutamine, diaminobenzylamine, and nicotinamide, wherein the amount of amine-oxidation inhibitor added to the oxidation-sensitive amine is in an amount ranging from 5 ppm to 5000 ppm.

2. The method of claim 1, further including storing the inhibitor-treated amine in a container padded with an inert gas.

3. The method of claim 1, further including incubating the inhibitor-treated amine at a temperature of from 0° C. to 150° C.

4. The method of claim 1, further including adding the inhibitor-treated amine to another oxidation-sensitive material selected from one or more of an isocyanate, a polyol, a prepolymer, a quasiprepolymer, and a blowing agent.

5. The method of claim 1, wherein the oxidation-sensitive amine is a tertiary amine catalyst selected from one or more of bis-(2-dimethyaminoethyl) ether, N, N, N'-trimethyl-N'-hydroxyethylbisaminoethylether, N-(3-dimethylaminopropyl)-N, N-diisopropanolamine, N,N-dimethylethanolamine, triethylene diamine, N, N-dimethylcyclohexylamine, benzyldimethylamine, pentamethyldiethylenetriamine, N, N, N',N,", N"-pentamethyldipropylenetriamine, N, N-bis(3-dimethylaminopropyl)-N-isopropanolamine, N'-(3-(dimethylamino)propyl-N, N-dimethyl-1,3-propanediamine, 2-(2-dimethylaminoethoxy)ethanol, N,N,N'-trimethylaminoethylethanolamine, N-ethylmorpholine, N-methylmorpholine, 4-methoxyethylmorpholine, N, N'dimethylpiperzine, 2,2'-dimorpholinodiethylether, 1,3,5-tris(3-(dimethylamino)propyl)-hexahydro-s-triazine, and 3-(2-(dimethylamino)ethoxy)propylamine.

6. The method of claim 1, wherein the oxidation-sensitive amine is a polyetheramine selected from one or more of a monoamine, a diamine, a polyether diamine, an unhindered diamine, and a triamine.

7. The method of claim 1, wherein the oxidation-sensitive amine is an ethyleneamine selected from one or more of ethylenediamine, diethylenetriamine, triethylenetetramine, tetraethylenepentamine, aminoethylpiperzine, aminoethylethanolamine, pentaethylenehexamine, hexaethyleneheptamine, and mixtures thereof.

8. The method of claim 1, wherein the oxidation-sensitive amine is a surfactant amine selected from one or more of a polyether monoamine, a hydrophobic monoamine, and a hydrophilic polyether monoamine.

9. A method of forming an inhibitor-treated amine comprising combining:
   (i) an oxidation-sensitive amine selected from one or more of an amine catalyst, a polyetheramine, an ethyleneamine, an alkoxylated amine, diethanolamine, N-methyldiethanolamine, triethanolamine, and a surfactant amine; with
   (ii) an amine-oxidation inhibitor, wherein the amine-oxidation inhibitor is a free-radical scavenger selected from one or more of allupurinol, propyl thiouracil, glutamine, diaminobenzylamine, nicotinamide, methimazole, phenyl methimazole, and derivatives of methimazole or phenyl methimazole,
   wherein the inhibitor-treated amine and the amine-oxidation inhibitor are combined to form a blend such that the total amount of amine-oxidation inhibitor in the blend is from greater than 0.5% to 10% by weight of the total blend.

* * * * *